United States Patent [19]

Cliffe

[11] Patent Number: 4,921,860
[45] Date of Patent: May 1, 1990

[54] QUINUCLIDYL- AND TROPANYL-PYRIDYL ETHERS AS 5-HT₃ RECEPTOR ANTAGONISTS

[75] Inventor: Ian A. Cliffe, Cippenham, England

[73] Assignee: John Wyeth and Brother, Limited, Maidenhead, England

[21] Appl. No.: 226,637

[22] Filed: Aug. 1, 1988

[30] Foreign Application Priority Data

Aug. 4, 1987 [GB] United Kingdom ............... 8718445

[51] Int. Cl.⁵ ............... C07D 451/06; C07D 453/00; A61K 31/46
[52] U.S. Cl. ............... 514/304; 514/305; 546/125; 546/133
[58] Field of Search ............ 546/125, 133; 514/304, 514/305

[56] References Cited

U.S. PATENT DOCUMENTS

| | | | |
|---|---|---|---|
| 4,585,866 | 4/1986 | Fozard et al. | 546/129 |
| 4,643,995 | 2/1987 | Engel et al. | 514/210 |

FOREIGN PATENT DOCUMENTS

| | | | |
|---|---|---|---|
| 0201165 | 3/1986 | European Pat. Off. | 546/125 |
| 0210840 | 4/1987 | European Pat. Off. | 548/337 |
| 0278173 | 12/1987 | European Pat. Off. | 546/112 |
| 2125398 | 3/1984 | United Kingdom | 546/125 |
| 2152048 | 7/1985 | United Kingdom | 546/125 |

OTHER PUBLICATIONS

Richardson et al., Nature, 316, 126-131 (1985).
Tell et al., Proceedings of the BPS, p. 279P (Apr. 1984).
Anderson et al., British Medical Journal, 294, 1129 (1987).
The Lancet, Jun. 27, 1987, p. 1470-1.
Tyers et al., Neuroscience Letters Suppl. 29, S68 (1987).
Costall et al., Br. J. Pharmacol., 90, 89P (1987).

*Primary Examiner*—Alan L. Rohman
*Attorney, Agent, or Firm*—Arthur G. Seifert

[57] ABSTRACT

Pyridyl ethers of formula

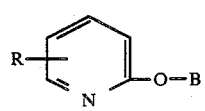

(II)

[where R is hydrogen, or 1 to 4 hydroxy, alkyl, alkoxy, amino, alkylamino, dialkylamino, halogen, trifluoromethyl, phenyl, halophenyl, alkyphenyl, alkoxyphenyl, carboxy, carboxamide, nitro, thiol or alkylthio substituents and B is quinuclidyl or tyopanyl] are useful for the treatment of conditions which respond to antagonism of 5 - HT₃ receptors e.g. the treatment of migraine, emesis, anxiety, gastro-intestinal disorders and psychotic disorders.

3 Claims, No Drawings

QUINUCLIDYL- AND TROPANYL-PYRIDYL ETHERS AS 5-HT$_3$ RECEPTOR ANTAGONISTS

The present invention relates to pyridyl ethers. More particularly it relates to methods of treatment involving the pyridyl ethers, to the use of such compounds in the preparation of a medicament, and to pharmaceutical compositions containing the compounds.

U.K Patent application No. 2152048A disclose compounds of the formula

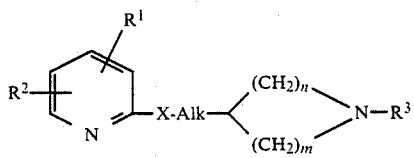

in which $R^1$ and $R^2$ can represent hydrogen or certain specified substituents, X represents oxygen, sulphur, SO or SO$_2$ Alk represents alkylene having from 0 to 4 carbon atoms and

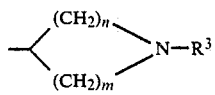

can represent inter alia a quinuclidyl or tropanyl radical.

The above mentioned U.K. application describes the compounds of formula (I) as having an analgesic and a hypotensive effect. We have now found that some of the compounds of formula I, and certain related pyridyl ethers, antagonise specific 5-hydroxytryptamine (5-HT) receptors, in particular 5-HT$_3$ receptors in warm blooded animals.

Accordingly, the present invention, in one aspect, provides the use of a pyridyl ether comprising a compound of the general formula

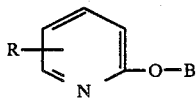

(where R represents hydrogen or 1 to 4 same or different substituents selected from hydroxy, C$_{1-6}$-alkyl, C$_{1-6}$-alkoxy, amino, C$_{1-4}$-alkylamino, di (C$_{1-4}$-alkyl) amino, halogen, trifluoromethyl, phenyl, halophenyl, C$_{1-4}$-alkylphenyl, C$_{1-4}$-alkoxyphenyl, carboxy, carboxamido, nitro, thiol and C$_{1-4}$-alkylthio and B represents quinuclidyl or tropanyl) or a N-oxide thereof or a pharmaceutically acceptable acid addition salt of the compound of formula (II) or the N-oxide, for the preparation of a medicament for the treatment of conditions which respond to antagonism of 5-HT$_3$ receptors.

In another aspect the invention relates to a method for the treatment of conditions in warm blooded animals (particularly humans) which respond to antagonism of 5-HT$_3$ receptors which method comprises administering to the warm blooded animal an effective amount of the pyridyl ether (as hereinabove defined).

5 HT$_3$ - antagonists have also been termed "antagonists of 'neuronal' 5-hydroxytryptamine receptors" and "serotonin (5-hydroxytryptamine) M receptor antagonists". Such compounds have been described as being useful inter alia in the treatment of migraine, emesis, anxiety, gastro intestinal disorders and psychotic disorders such as schizophrenia.

Accordingly in a further aspect the invention provides the use of a pyridyl ether (as hereinabove defined) for the preparation of a medicament for the treatment of migraine, emesis, anxiety, gastro-intestinal disorders or psychotic disorders. The invention also provides a method for the treatment of migraine, emesis, anxiety, gastro-intestinal disorders or psychotic disorders which comprises administering to a warm blooded animal in need thereof, an effective amount of the pyridyl ether (as hereinabove defined).

For certain of the above mentioned conditions it is clear that the pyridyl ethers may be used prophylactically as well as for the alleviation of acute symptoms. References herein to "treatment" or the like are to be understood to include such prophylactic treatment, as well as treatment of the acute conditions.

The anti-emetic properties of the pyridyl ethers are particularly advantageous in the treatment of nausea and vomiting associated with cancer chemotherapeutic agents and radiation therapy. The compounds are thereof of use in the treatment of cancer by chemotherapeutic agents (cytotoxic or cytostatic agents such as cisplatin, doxorubicin and cyclophosphamide) as well as irradiation. Accordingly, the invention also provides a product containing a cancer chemotherapeutic agent and a pyridyl ether (as defined above) as a combined preparation for simultaneous, separate or sequential use in cancer therapy.

In the compounds of formula (II), B is preferably quinuclid-3-yl or more preferably a tropan-3-yl radical. The latter is also termed an endo-8-methyl 8-azabicyclo[3.2.1]octyl radical. In the compounds any alkyl group is preferably methyl, ethyl, propyl, or butyl, any alkoxy group is preferably methoxy, ethoxy or propoxy and any halogen is preferably fluorine, chlorine or bromine.

The group R in the compounds of formula (I) is preferably hydrogen or one to four same or different substituents (preferably one or two substituents) selected from C$_{1-4}$-alkyl, C$_{1-4}$-alkoxy, halogen (particularly chlorine) nitro and carboxamido.

Certain of the compounds of formula II do not fall within formula I above of U.K. specification 2152048 A whilst others are not disclosed specifically in the UK. specification. Accordingly the present invention also provides the following specific compounds:

endo-8-methyl-3-(2-pyridyloxy) 8-azabicyclo [3.2.1]octane endo 8-methyl 3 (6-methyl 2 pyridyloxy)-8-aza bicyclo [3.2.1]octane endo-8-methyl-3-(5 methyl-2-pyridyloxy) 8-azabicyclo[3.2.1]octane 3-(2-pyridyloxy)-1-azabicyclo[2.2.2]octane and their pharmaceutically acceptable acid addition salts.

The compounds of formula (II) may be prepared by methods known for the preparation of ethers such as those disclosed in U.K. Application No. 2152048 A. For example, a pyridine derivative of formula

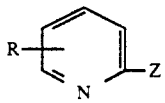

(III)

or a N-oxide thereof may be condensed with a compound of formula $$Z^1\text{-B} \qquad \qquad (IV)$$

where R and B are as defined above and one of Z and $Z^1$ is hydroxy and the other is a leaving group such as halogen, $C_{1-6}$-alkysulphonyloxy (e.g. methylsulphonyloxy) or arysulphonyloxy where the aryl radical may be, for example, phenyl or naphthyl optionally substituted by $C_{1-4}$-alkyl (e.g. p-toluenesulphonyloxy). Preferably Z is a leaving group, particularly halogen, and $Z^1$ is hydroxy. The condensation may be carried out in the presence of a condensing agent, particularly a basic condensing agent such as an alkali metal or alkaline earth metal hydroxide or carbonate, potassium or sodium hydride, phenyl- or an alkyl lithium (e.g. butyllithium), an alkali metal amide (e.g. lithium diisopropylamide) or an organic base such as tertiary amine, pyridine or piperidine. The condensation may be carried out in an organic solvent. The anion of the alcohol may be first prepared by reaction of the alcohol with a strong base and the anion may subsequently be reacted with the second reactant containing the leaving group.

It will be realised that if the pyridine derivative (III) contains groups that would be affected under the reaction conditions employed for the condensation reaction such groups may be protected and the protecting group subsequently removed. For example, hydroxy groups may be protected by formation of acetals or ethers (e.g. benzyl or silyl ethers) and amino groups may be protected by formation of urethanes or N-benzyl derivatives.

The compounds of formula (II) may be converted into their N oxides by methods known for analogous compounds. For example, the compounds of formula (II) may be oxidised, e.g. in an inert solvent with a peracid (e.g. peracetic acid, perbenzoic acid or m-chloroperbenzoic acid), hydrogen peroxide, an alkali metal peroxide or an alkyl peroxide.

The starting materials of formulae (III) and (IV) are described in the literature or may be prepared by methods known for analogous compounds.

If in the processes described above the pyridyl ether is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic and p toluenesulphonic acids.

The pyridyl ethers are tested for 5-$HT_3$ receptor antagonism in the isolated vagus nerve of the rat by a method based upon that of Ireland S. J. and Tyers M. B. Brit. J. Phamacol., 1987, 90, 229–238. The procedure relies upon the ability of 5-HT to induce depolaraisation of neurones in the cervical vagus nerve by a direct action of 5-$HT_3$ receptors. A concentration response curve to 5-HT induced depolaraisation is obtained and the antagonists are added to the bath containing the isolated nerve before repeating the 5-HT concentration-response curve. Antagonist potency is estimated from the 5-HT concentration ratios and expressed as an apparent $pK_B$ value (where $K_B$ is the antagonist dissociation constant). When tested by this procedure endo 8 methyl-3 (2-pyridinyloxy)-8-azaabicyclo[3.2.1] octane. a representative compound of formula I, had a $pK_B$ of 6.2.

The compounds of the invention are also tested for 5-$HT_3$ antagonistic activity in the isolated right atrium of the rabbit heart based upon the method of Fozard J. R., Naunyn-Schmiedeberg's Arch. Pharmacol., 1984, 326, 36–44. The procedures relies upon the ability of 5-HT to stimulate 5-$HT_3$ receptors present on sympathetic nerve terminals in the heart, causing release of noradrenaline which evokes an increase in the spontaneous rate of breathing. The antagonist potency is expressed in a similar manner to that of the preceding test method i.e. as an apparent $PK_B$. When tested by this procedure endo-8-methyl-3-(pyridinyloxy)-8-azabicyclo[3.2.1]octane had a $PK_B$ of 7.4.

The pyridyl ethers may be administered in association with a pharmaceutically acceptable carrier. Any suitable carrier known in the art can be used to prepare the pharmaceutical composition. In such a composition, the carrier is generally a solid or liquid or a mixture of a solid and a liquid.

Solid form composition include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in a mixture with the finely divided active ingredient. carrier having the necessary compression properties in suitable proportions and compacted in the shape and size desired. The powders and tablets preferably contain up to 99%, e.g. from 0.03 to 99% preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquids form compositions include, for example, solutions, suspensions, emulsions, syrups, elixers and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solibilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parental administration.

Liquid pharmaceutical compositions which are sterile solutions or suspensions can be utilized by, for example, intramuscular, intraperitioneal or subcutaneous injection. Sterile solutions can also be administered intravenously. When the compound is orally active it can be administered orally either in liquid or solid composition form.

The compounds of the invention can also be administered by the nasal route. When formulated for nasal administration the compositions may comprise a compound of the invention in a liquid carrier; such compositions may be administered for example in the form of a spray or as drops. The liquid carrier may be water (which may contain further components to provide the desired isotonicity and viscosity of the composition). The composition may also contain additional excipents such as preservatives, surface active agents and the like. The compositions may be contained in a nasal applicator that enables the composition to be administered as drugs or as a spray. For administration from an aerosol container the composition should also include a propellant.

Preferably the pharmaceutical composition is in unit dosage form, e.g. as tablets or capsules. In such form, the composition is sub-divided in unit doses containing appropriate quantities of the active ingredient; the unit dosage forms can be packaged composition, for example packeted powders, vials, ampoules, prefilled syringes or sachets containing liquids. The unit dosage form can be, for example, a capsule or tablet itself, or it can be the appropriate number of such compositions in package form. The quantity of the active ingredient in unit dose of composition may be varied or adjusted from 0.5 mg or less to 750 mg or more, according to the particular need and the activity of the activity ingredient. The invention also includes the compounds in the absence of the carrier where the compounds are in unit dosage form.

The following Examples illustrate the invention. The Reference Example illustrates the preparation of a known compound which is disclosed in UK Application 2152048A.

EXAMPLE 1

Endo 8 methyl-3-(2-pyridinyloxy)-8-azabicyclo[3.2.1]octane

A solution of tropine (8.8 g, 62.5 mmol) in dry tetrahydrofuran (25 ml) at 0° was treated with 1.27 M-BuLi in hexane (50 ml) under nitrogen, warmed to room temperature, treated with 2-bromopyridine (6 ml, 62.9 mmol) in dry dimethyl formamide (100 ml), stirred at 90° for 4d, cooled to room temperature, and poured into water (500 ml). The mixture was extracted with chloroform (2×400 ml) and the extracts were washed with water (3×800 ml), dried (magnesium sulphate), and evaporated in vacuo to give an oil which was purified by chromatography (alumina; ether). The yellow liquid was dissolved in ether and acidified with ethereal hydrogen chloride. The oil obtained after evaporation in vacuo was crystallised from propan-2-olethyl acetate and dried in vacuo at 50° to give the title compound as the dihydrochloride (2.6 g), m.p. 204°–5° (dec). (Found: C, 53.3; H, 7.0; N, 9.5. $C_{13}H_{18}N_2O.2HCl$ requires C, 53.6; H, 6.9; N, 9.6%).

EXAMPLE 2

Endo-8-methyl-3-(6-methyl 2-pyridyloxy)-8-azabicyclo [3.2.1]octane.

A stirred solution of tropine (6.2 g, 44.0 mmol) in dry dimethyl sulphoxide (100 ml) was treated with sodium hydride, 50% dispersion in oil (2.3 g containing ca. 47.9 mmol sodium hydride) under nitrogen. After 30 min, the solution was treated with 6-chloro-2-picoline (5.4 ml, 49.4 mmol), heated at 90° for ½h, cooled to room temperature, treated with water (200 ml), and extracted with ethyl acetate (2×100 ml). The organic phases were combined and extracted with 0.25 N HCl (200 ml). The aqueous extract was washed with ethyl acetate (2×200 ml), basified with sodium hydroxide and extracted with ethyl acetate (2×200 ml). The extracts were dried (magnesium sulphate) and evaporated in vacuo to give a yellow liquid. The liquid was converted into the hydrochloride salt with ethereal hydrogen chloride and methanol. The salt was recrystallised from ethyl acetate methanol to give the title compound as the dihydrochloride (3.7 g) m.p. 232°–234°. (Found: C, 54.4; H, 7.3; N, 9.0. $C_{14}H_{20}N_2O.2HCl. \frac{1}{4}H_2O$ requires C, 54.3; H, 7.5; N, 9.0%).

EXAMPLE 3

Endo-8-methyl-3-(5-methyl 2-pyridyloxy)-8-azabicyclo [3.2.1]octane

This compound was prepared by the method employed in Example 2.

Tropine (5.3 g, 37.6 mmol), 2-bromo-5-methylpyridine (7.1 g, 41.3 mmol), and sodium hydride, 50% dispersion in oil (2.0 g) was heated in dimethyl sulphoxide (100 ml) at 90° for 30 minutes. Standard work-up, column chromatography (alumina; ether), conversion to the dihydrochloride salt, and recrystallisation from ethyl acetate methanol gave the product as the dihydrochloride (2.05 g), m.p. 217°–219°. (Found: C, 56.4; H, 7.5; N, 8.6. $C_{14}H_{20}N_2O$ 2HCl $H_2O$ requires C,52.0, H 7.5; N, 8.7%).

EXAMPLE 4

3-(2-Pyridyloxy)-1 azabicyclo[2.2.2]octane

This compound was prepared by the method in Example 2.

The 3 day reaction of 3-quinuclidinol (5.32 g, 41.8 mmol), 2-fluoropyridine (4.00 ml, 46.5 mmol), and sodium hydride, 50% dispersion in oil (2.25 g) gave the product as a yellow oil.

The one and a half hydrochloride salt was isolated as colourless crystals (7.3 g), m.p. 204°–215° (dec) (from methanol-ethyl acetate).

(Found: C, 56.2; H, 6.7; N, 10.6. $C_{12}H_{16}N_2O$ 1½ HCl requires C, 55.7; H, 6.8; N, 10.8%).

REFERENCE EXAMPLE

Endo-8-methyl-(6-chloro-2-pyridyloxy)-8-azabicyclo [3.2.1]octane

The compound was prepared from 2,6-dichloropyridine (6.2 g, 41.9 mmol), tropine (5.35 g, 37.9 mmol), and sodium hydride, 50% dispersion in oil (2.0 g) using the method described in Example 2.

The hydrochloride salt of the product was prepared in methanol-ether and was recrystallised from methanol-ethyl acetate to give colourless crystals (6.01 g), m.p. 264°–266° (dec) (Found: C, 54.0; H, 6.3; N, 10.2. $C_{13}H_{17}C\ N_2O$. HCl requires C, 54.0; H, 6.3; N, 9.7%).

I claim:

1. A method for the treatment of conditions in warm blooded animals which respond to antagonism of 5-HT$_3$ receptors which method comprises administering to the warm blooded animal an amount effective to alleviate such condition of a pyridyl ether comprising a compound of formula

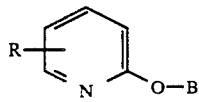

wherein R represents hydrogen or 1 to 4 same or different substitutes selected from hydroxy, $C_{1-6}$-alkyl, $C_{1-6}$-alkoxy, amino, $C_{1-4}$-alkylamino, di($C_{1-4}$-alkyl)-amino, halogen, trifluoromethyl, phenyl, halophenyl, $C_{1-4}$-alkylphenyl, $C_{1-4}$-alkoxyphenyl, carboxy, carboxamido, nitro, thiol and $C_{1-4}$-alkylthio and B represents quinuclidyl or tropanyl or a N-oxide thereof or a pharmaceutically acceptable acid addition salt of the compound of formula (II) or the N-oxide.

2. A method for the treatment of migraine, emesis, anxiety, gastrointestinal disorders or psychotic disorders in warm blooded animals which comprises administering to the warm blooded animal an amount effective to alleviate such condition of a pyridyl ether comprising a compound of formula

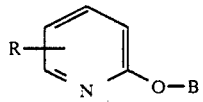

where R represents hydrogen or 1 to 4 same or different substitutes selected from hydroxy, $C_{1-6}$-alkyl, $C_{1-6}$-alkoxy, amino, $C_{1-4}$-alkylamino, di($C_{1-4}$-alkyl)-amino, halogen, trifloromethyl, phenyl, halophenyl, $C_{1-4}$-alkylphenyl, $C_{1-4}$-alkoxyphenyl, carboxy, carboxamido, nitro, thiol and $C_{1-4}$-alkylthio and B represents quinuclidyl or tropanyl or a N-oxide thereof or a pharmaceutically acceptable acid addition salt of the compound of formuls (II) or the N-oxide.

3. The method as claimed in claim 1 or claim 2 in which the pyridyl ether is
endo-8-methyl-3-(2-pyridyloxy) 8-azabicyclo[3.2.1]octane
endo-8-methyl-3-(6-methyl-2-pyridyloxy)-8-aza bicyclo[3.2.1]octane,
endo-8-methyl-3-(5-methyl-2-pyridyloxy)-8-aza bicyclo[3.2.1]octane,
3-(2-pyridyloxy)-1-azabicyclo[2.2.2]octane,
endo-8-methyl-(6-chloro-2-pyridyloxy)-8 azabicyclo[3.2. 1]octane
or a pharmaceutically acceptable acid addition salt thereof.

* * * * *